(12) United States Patent
Hegmann et al.

(10) Patent No.: US 10,568,986 B2
(45) Date of Patent: Feb. 25, 2020

(54) BIOCOMPATIBLE SMART RESPONSIVE SCAFFOLD HAVING INTERCONNECTED PORES

(71) Applicant: Kent State University, Kent, OH (US)

(72) Inventors: Elda Hegmann, Kent, OH (US); Torsten Hegmann, Kent, OH (US); Yunxiang Gao, Kent, OH (US)

(73) Assignee: KENT STATE UNIVERSITY, Kent, OH (US)

( * ) Notice: Subject to any disclaimer, the term of this patent is extended or adjusted under 35 U.S.C. 154(b) by 281 days.

(21) Appl. No.: 15/106,468

(22) PCT Filed: Dec. 19, 2014

(86) PCT No.: PCT/US2014/071618
§ 371 (c)(1),
(2) Date: Jun. 20, 2016

(87) PCT Pub. No.: WO2015/095768
PCT Pub. Date: Jun. 25, 2015

(65) Prior Publication Data
US 2016/0339145 A1 Nov. 24, 2016

Related U.S. Application Data

(60) Provisional application No. 61/918,084, filed on Dec. 19, 2013.

(51) Int. Cl.
*A61L 27/56* (2006.01)
*C09K 19/38* (2006.01)
(Continued)

(52) U.S. Cl.
CPC .......... *A61L 27/18* (2013.01); *A61L 27/3834* (2013.01); *A61L 27/54* (2013.01); *A61L 27/56* (2013.01);
(Continued)

(58) Field of Classification Search
CPC .......... A61L 27/18; A61L 27/54; A61L 27/58; A61L 2400/08; C12N 2537/10; C09K 2219/00
See application file for complete search history.

(56) References Cited

PUBLICATIONS

Nagahama et al. "Temperature-Induced Hydrogels Through Self-Assembly of Cholesterol-Substituted Star PEG-b-PLLA Copolymers: An Injectable Scaffold for Tissue Engineering." 2008. Advanced Functional Materials. vol. 18, pp. 1220-1231. (Year: 2008).*
(Continued)

*Primary Examiner* — Kara B Boyle
(74) *Attorney, Agent, or Firm* — Renner Kenner Greive Bobak Taylor and Weber; Ray Weber; Tim Hodgkiss

(57) ABSTRACT

A polymeric scaffold contains pendant liquid crystal side chains and has fully interconnected pores. Such a polymeric scaffold will preferably be 3D in nature and elastomeric, biocompatible and biodegradable. Such 3D liquid crystal elastomer (LCE) scaffolds can be used for various biomedical applications, including cell culture applications. A method for the production of such a polymeric scaffold containing liquid crystals and having interconnected pores is also disclosed that uses a metal foam sacrificial template as a scaffold to produce the polymeric smart response scaffold of the present invention. Consistent and controlled pore sizes result from etching the sacrificial metal foam template away from the polymeric scaffold, permitting the incorporation of growth factors, when needed, for enhancing cell viability and proliferation.

26 Claims, 7 Drawing Sheets

(51) Int. Cl.
  *A61L 27/18* (2006.01)
  *C08G 63/682* (2006.01)
  *A61L 27/38* (2006.01)
  *A61L 27/54* (2006.01)
  *A61L 27/58* (2006.01)
  *C08J 9/26* (2006.01)
  *C12N 5/00* (2006.01)

(52) U.S. Cl.
  CPC .......... *A61L 27/58* (2013.01); *C08G 63/6822* (2013.01); *C08J 9/26* (2013.01); *C09K 19/3833* (2013.01); *C09K 19/3838* (2013.01); *C12N 5/0062* (2013.01); *A61L 2300/63* (2013.01); *A61L 2400/00* (2013.01); *A61L 2400/08* (2013.01); *C08J 2201/0442* (2013.01); *C08J 2207/10* (2013.01); *C08J 2367/04* (2013.01); *C09K 2219/00* (2013.01); *C12N 2533/30* (2013.01); *C12N 2537/10* (2013.01)

(56) References Cited

PUBLICATIONS

Ilagan et al., "Macroporous photocrosslinked elastomer scaffolds containing microporosity: Preparation and in Vitro degradation properties," Journal of Biomedical Materials Research Part A. vol. 93A, Issue 1. Apr. 2010. pp. 211-218. (Year: 2010).*

Zhou et al., "Polymers Comprising Cholesterol: Synthesis, Self-Assembly, and Applications," Materials, 2009, 2. pp. 636-660. (Year: 2009).*

Van de Manakker et al. "Rheological behavior of self-assembling PEG-β-cyclodextrin/PEG-cholesterol hydrogels," Langmuir 2008, 24, pp. 12559-12567. (Year: 2008).*

* cited by examiner

BIOCOMPATIBLE SMART RESPONSIVE SCAFFOLD HAVING INTERCONNECTED PORES

CROSS-REFERENCE TO RELATED APPLICATION

This application claims the benefit of U.S. Provisional Application No. 61/918,084 filed Dec. 19, 2013, the contents of which are incorporated herein by reference.

TECHNICAL FIELD

The present invention relates to polymeric scaffolds. More particularly, the present invention relates to polymeric scaffolds containing liquid crystal materials and having fully interconnected pores. Even more specifically, the present invention relates to polymeric and biocompatible smart response scaffolds (SRSs) that respond to external stimuli and that are based on elastomers formed from three-arm star block copolymers (SBC) having pendant liquid crystal side chains.

BACKGROUND OF THE INVENTION

Stem cells are known to have the remarkable ability to develop into many different cell types of a living body, such as a human or animal, during the early life and growth of the cells. Stem cells also serve as internal repair systems for many organ tissues, and serve to replenish other cells, as long as the organ-carrier (e.g., humans, animals) is still alive.

The combination of the use of stem cells with polymeric scaffolds is a promising strategy for tissue engineering and for cellular delivery. With respect to tissue engineering applications, several types of scaffolds have been used in combination with stem cells. Such scaffold materials are generally classified as natural or synthetic, with each having distinct advantages and drawbacks.

Several natural or biocompatible synthetic materials have been developed for specific scaffold applications. For example, many scaffold materials are based on proteins, such as fibrin and silk; polysaccharides, such as agarose and alginate; polymers, such as PEG (polyethylene glycol); peptides; or ceramic materials. Due to their chemical nature, these scaffold materials have been studied for use in forming bone, cartilage, heart, nerve, retinal, and vasculature tissue structures. Furthermore, these scaffold materials can be utilized in the directed differentiation of stem cells into mature phenotypes or can be used for the expansion of undifferentiated stem cells.

However, none of these developments in scaffold technology have resulted in a smart responsive scaffold (SRS) or biocompatible scaffold that can, by choice, respond to a variety of external stimuli, such as temperature, applied fields (e.g., electric field, magnetic field), surface alignment, or mechanical deformation (i.e., stress/strain) with a macroscopic ordering event (e.g., an increase in order).

The advantages of using cell delivery for therapeutic applications are significant. However, it is the methods of administration that are an important key for the success of the treatments sought, such as injecting the dispersion of cells directly into injured sites. To that end, various approaches have also been used to encapsulate cells in polymer matrices for delivery to an injured site. For example, hydrogels were thought to be attractive due to their potential in maintaining cell viability. Unfortunately, they do not offer the necessary mechanical support. Other approaches have focused on the use of porous beads for the purpose of cell delivery. In this approach, beads are cell-loaded and cultured in a medium prior to being placed or injected directly into the affected or diseased site. While beads and hydrogels may also contain bioactive agents (e.g., growth factors, proteins) they do not guide cells to differentiate into a particular cell lineage. Furthermore, because extreme care should be taken in the choice of cells to be implanted, it is of paramount importance to ensure that cells will differentiate into the desirable lineage by 'copying' surrounding cells. If there is heterogeneity of cells at the sites sought for repair, it will ultimately be difficult to predict that the cells will respond as desired. In addition, some scaffolds made of natural polymers (e.g., fibrin or collagen) have difficulty when used in the area of tissue regeneration because of necrosis (i.e., cell death) found at the center of these scaffolds. As a result, such scaffolds provide diminished mechanical properties and instability, which is undesirable.

Elastomers, however, have gained considerable attention for their use in forming scaffold because they offer many advantages over tough, rigid polymers. Most importantly, the physical properties of elastomers can be tuned in a way that they can withstand applied mechanical forces, such as strain, stress, and impacts, because they are soft and deformable. In addition, elastomers have been found to be suitable as carriers for drug delivery applications. Biodegradable elastomers have been mainly made of two types: thermoplastics and thermosets. Thermoplastics are easily made, but degrade heterogeneously due to the presence of crystalline and amorphous regions within the material. This leads to a rapid loss of mechanical strength. While thermosets are not as easily prepared, they offer more uniform biodegradation rates, better mechanical properties, and improved chemical resistance.

Accordingly, smart responsive scaffolds (SRSs) that respond to external stimuli resulting in a macroscopic ordering event have been developed by at least one or more inventors in this application and are disclosed in PCT Patent Application Publication No. WO 2014/172261, the disclosure of which is incorporated herein by reference. These unique, smart responsive scaffolds (SRSs) utilize thermoset elastomers that are based on three-arm star block copolymers (SBCs) using ring opening polymerization of suitable monomers followed by cross-linking to form the elastomer. Since their discovery, these biocompatible and biodegradable elastomers have become an important factor in the fabrication of modern biomedical technologies, such as tissue engineering and drug delivery. Their elastomeric characteristics not only mimic the mechanical deformation of the biological supporting matrix, but also facilitate cell interaction by modulating cellular behavior. Among the biodegradable elastomeric soft materials that have been developed, the polycaprolactone (PCL)-Polylactide acid (PLA)-based elastomers have become ideal for use in these biomedical applications due to their known biocompatibility and biodegradability. The star-shaped block copolymer (SBC) of PCL with other biocompatible blocks, such as Polylactide (PLA), offer multiple polymer arms for better controlled elasticity and degradability. PCL-based scaffolds are well known and are one of the most commonly used materials for such new biomedical applications.

Unfortunately, while the new three-arm star block copolymer with liquid crystal side chain-based elastomeric films have shown promise in targeting on aligned cell culturing with the guidance of liquid crystal behaviors, there are limitations on the elastomeric films' ability to maximize the performance of the elastomeric scaffold for better cell culturing applications. That is, the performance of the material as an elastomeric scaffold remains limited by any of a number of issues, including the composition of the star block copolymers, the molecular structure of the cross-link sites and morphology of the scaffold itself.

For example, the current smart responsive scaffolds (SRSs), while porous, do not contain any interconnecting pores. That is, the pores of these three-arm star block copolymer-based scaffold materials having pendant liquid crystal side chains do not develop well-defined, interconnected pores, and instead, only have pores that provide for additional surface area for cell migration, but do not allow for a well-defined porosity with interconnected pores that will allow for better tissue development and improved cell adherence and growth. It is well known in the art that, in order to effectively utilize the elastomer-based scaffolds with liquid crystal side chains for tissue engineering and biomedical applications, the scaffolds must have well-defined porosity and surface properties that provide support for cell adherence, growth, and mass transport of the nutrients/waste in and out of the scaffold pores under physiological conditions.

There are at least three types of mass transport to be considered for three-dimensional (3D) cell cultures: (a) oxygen mass transport (i.e., controlling metabolism rate), (b) mass transport of nutrients to cells, and (c) waste mass transport (i.e., eliminating toxins that, for example, raise pH to toxic levels, among others). Just as important, controlled porosity of the elastomer promotes 3D cell-elastomer interactions, space for extracellular matrix (ECM) formation and the possibility of linking molecular entities to allow binding of cell growth factors or other proteins to enhance cellular adhesion and ECM formation.

Chemical and photo-initiated cross-linking of linear polymer precursors or multi-arm polyester precursors, also known as star shaped copolymers, have been used as methods for designing porous polymeric materials for biomedical applications, but these methods only provide pores and do not actively promote controlled porosity or interconnecting pores. Such methods for the preparation of porous elastomers are rare. One example includes the incorporation of a leachable solid, such as paraffin beads, into a polymer and draining it after forming porous elastomer materials. Other methods include the use of a solvent vapor annealing method developed to prepare thin films of block copolymers with well-defined porosity.

Despite many advantages, these methods still have certain limitations. For example, photo-initiated cross-linking is limited to polyesters and requires an extra step to attach an unsaturated moiety to polymers prior to cross-linking. This is both time consuming and costly.

Thus, instead of fabricating elastomer films, developing liquid crystal elastomeric foams for high-efficiency cell culture offers the promise of higher efficiency and new tissue engineering functions. These scaffold foams will enable the mass transport of oxygen and nutrients important to the development of healthy cells as well as enable the rapid flushing of wastes from the scaffold to prevent degradation of the cell culture.

Fabrication of porous (i.e., containing pores) elastomer scaffolds has been previously attempted, and various methods have been pursued. For example, porous foam has been made using a micelle template, but the pore size is usually limited to only a few microns due to the size of the micelles used. Other scaffolds have been built up with microfibers generated by electrospun templates, or gas bubble templates, but these do not provide for adequate control and consistency of the porosity.

Thus, the need exists for alternative 3D scaffolds that provide suitable pores sizes that are both controlled and consistent. For some applications, hollowed, channeled scaffolds are desired for mimicking vascular conduits within a body. However, most of these hollowed channel fabrications rely on lithography and require time-consuming and equipment-demanding experiment conditions. Furthermore, many of these channeled scaffolds are only simplified models of the vascular conduits in vivo, consisting of aligned channel arrays due to their relatively-easy fabrication. The need to produce more complex networks and scaffolds having interconnected pores in the range of between 100 microns and 500 microns, and/or micro-channels of similar, or slightly larger, size in a simple and convenient way continues to exist.

SUMMARY OF THE INVENTION

In general, the present invention provides a polymeric scaffold containing liquid crystals and having fully interconnected pores. Such a polymeric scaffold will preferably be 3D in nature and elastomeric. Such 3D liquid crystal elastomer (LCE) scaffolds can be used for various biomedical applications, including cell culture applications. A method for the production of such a polymeric scaffold containing liquid crystals and having interconnected pores is also provided.

Advantageously, the method employs the use of sacrificial metal (e.g., nickel) foam templates having various pore sizes to control the interconnected porosity and the pore size of the elastomeric, polymeric scaffold. Beyond being easy and efficient to manipulate, the present invention also provides different polymer casting strategies to control the morphology of the product to be either a scaffold with channel networks (truly interconnected channeled network) or a 3D foam made up polymer mesh network (primary-level porosity) with the polymer mesh being completely hollowed (secondary level porosity).

Further advantages of the present invention include a smart responsive scaffold (SRS) that responds to external stimuli resulting in a macroscopic ordering event. Another advantage of the present invention is that a smart responsive scaffold (SRS) is formed of elastomers having increased pore size so they can be used for a wide selection of cells, as well as permitting the incorporation of growth factors, when needed, for enhancing cell viability and proliferation. Yet another advantage of the present invention is that a smart responsive scaffold (SRS) is formed with elastomers that have a pore size that provides for fully interconnected pores that allows for the holding of a desirable load (e.g. a dye), which will leach out under pressure or that will encapsulate a temperature-sensitive liquid crystal mixture (e.g. cholesteric temperature sensors).

Further advantages of the present invention over the known art relating to polymeric scaffolds, and particularly, smart response scaffolds, which shall become apparent from the specification that follows, are accomplished by the invention as hereinafter described and claimed.

In general, the present invention provides a polymeric scaffold containing liquid crystals and having fully interconnected pores. In one embodiment, the polymeric scaffold, as above, includes a star block copolymer having pendant liquid crystal side chains. The star block copolymer includes a core derived from a polyol, such as, for example, glycerol, pentaerythritol, or dipentaerythritol, and a plurality of arms of random block copolymers. In one embodiment, the arms of the random block copolymer include one or more polymer blocks derived from halide-substituted lactone monomers; one or more polymer blocks derived from lactone monomers or isomers thereof; and one or more polymer blocks derived from lactide monomers, wherein at least one of the one or more polymer blocks derived from the halide-substituted lactone monomers of each arm contains a liquid crystal pendant from the polymer block at the position where the halide was originally substituted. In one embodiment, the liquid crystal may be selected from a cholesterol-based chiral nematic liquid crystal and derivatives thereof, a cholesteryl liquid crystal and derivatives thereof; and a 3,4-difluoropentyl-bicyclohexyl-base nematic liquid crystal and derivatives thereof. In one or more embodiments, the polymeric scaffold as above includes the interconnected pores having a diameter ranging from about 50 microns to about 700 microns. In another embodiment, the diameter of the interconnected pores range from 100 microns to 500 microns. In yet another embodiment, the polymeric scaffold above may further include non-interconnected pores ranging in diameter of from 5 microns to 700 microns. In still other embodiments, the non-interconnected pores may range from 5 microns to 500 microns in diameter.

As noted above, the polymeric scaffold may be elastomeric, biocompatible, and/or biodegradable.

In one or more of the above embodiments that can employ a star block copolymer, the star block copolymer may be crosslinked by a crosslinking agent to form a thermoset elastomer, wherein the crosslinking agent is a compound that is biocompatible and biodegradable with the star block copolymer. In one or more these embodiments, the crosslinking agent may be selected from the group consisting of 2,2-bis(1-caprolactone-4-yl) propane (BCP) and derivatives thereof, and bis-caprolactone with oligoethylene glycol spacer and derivatives thereof.

In still other embodiments of the above scaffold, the scaffold may include fully interconnected pores and fully interconnected channels, the fully interconnected pores forming hollow passages within the framework of the polymeric scaffold.

It will be appreciated that the scaffold of the present invention, as disclosed in any embodiment above, may be adaptable for use in combination with stem cells for tissue engineering and cell delivery. In one or more of the above embodiments, the scaffold is a biocompatible, smart responsive scaffold responsive to external stimuli. For purposes of this invention, the term "external stimuli" means any outside stimulus that will affect a change of the liquid crystal. Such stimuli include temperature, applied fields (e.g., electric, magnetic), surface alignment, mechanical deformation (i.e., stress/strain) with a macroscopic ordering event (e.g., an increase in order), light (any wavelength), changes of pH, and the presence of chemicals.

The present invention also provides a method for the production of a polymeric scaffold containing liquid crystals and having interconnected pores, the method including providing a metal foam scaffold template, casting a liquid crystal-containing polymeric material around the metal foam scaffold template, crosslinking the casted liquid crystal-containing polymeric material and metal foam scaffold template to provide a polymeric scaffold around the metal foam scaffold template to form a crosslinked scaffold, and etching the metal foam scaffold template to remove the metal foam scaffold template embedded within the crosslinked scaffold and to provide a polymeric scaffold containing liquid crystals and having interconnected pores where the metal foam scaffold template was removed.

In one or more embodiments, the liquid crystal-containing polymeric material is a star block copolymer having pendant liquid crystal side chains. In those embodiments, the star block copolymer can include a core derived from a polyol and a plurality of arms of random block copolymers. The arms of random block copolymers may include one or more polymer blocks derived from halide-substituted lactone monomers; one or more polymer blocks derived from lactone monomers or isomers thereof; and one or more polymer blocks derived from lactide monomers, wherein at least one of the one or more polymer blocks derived from the halide-substituted lactone monomers of each arm contains a liquid crystal pendant from the polymer block at the position where the halide was originally substituted.

It will be appreciated that there is more than one way to cast the liquid crystal-containing polymeric material around the metal foam scaffold template. In both embodiments, the step of casting includes initially immersing the metal foam scaffold template into the liquid crystal-containing polymeric material. However, in one instance, the metal foam scaffold template is left in liquid crystal-containing polymeric material until a suitable crosslinked scaffold is obtained. In the other instance, the metal foam scaffold template is removed or taken out of the liquid crystal-containing polymeric material either before or during the crosslinking step. This latter method has been referred to herein as "dipping" the metal foam scaffold template into the liquid crystal-containing polymeric material. In some embodiments extending form this "dipping" step, the step of casting further includes removing the metal foam scaffold template from the liquid crystal-containing polymeric material before crosslinking so as to provide channels within the polymeric scaffold upon crosslinking, the channels being defined by the voids within the metal foam scaffold template. In other embodiments, the step of casting further includes removing the metal foam scaffold template from the liquid crystal-containing polymeric material during crosslinking so as to provide at least some channels within the polymeric scaffold upon crosslinking, the channels being defined as smaller than the original voids within the metal foam scaffold template.

In another alternative method for casting, the step of casting includes the step of pouring the liquid crystal-containing polymeric material over the metal foam scaffold template.

For the crosslinking step, in one or more embodiments, the step of crosslinking includes crosslinking with a crosslinking agent to form a thermoset elastomer, wherein the crosslinking agent is selected from the group consisting of 2,2-bis(1-caprolactone-4-yl) propane (BCP) and derivatives thereof, and bis-caprolactone with oligoethylene glycol spacer and derivatives thereof. In one or more of these same embodiments, the step of crosslinking further includes heating the casted liquid crystal-containing polymeric material and metal foam scaffold template to at least 140° C.

With more particular attention to the step of etching the metal foam scaffold template, the step may include removing the metal foam scaffold template by immersing the crosslinked scaffold in a saturated $FeCl_3$ solution. Such a solution is a known etchant and will remove metals such as nickel or iron oxide that forms the metal foam scaffold template from the crosslinked scaffold. It will first be appreciated that any metal or alloy can be used as the metal foam scaffold template, provided such a metal foam scaffold template can be produced and removed by a known etchant.

Examples of possible metals or alloys other than the nickel and iron oxide metals noted above, which can be used include, but are not necessarily limited to, aluminum alloys, low and high carbon steel, brasses and bronzes, stainless stain, cast iron, tin alloys, copper alloys, zinc alloys, and ceramics. Correspondingly, there are a number of etchants that can be used instead of the proposed $FeCl_3$ solution above. These etchants include, but are not limited to, ammonia hydrogen peroxide solutions (used to etch copper alloys), $CuCl_2$ solutions, hydrochloric acid solutions, hydrofluoric acid solutions, ethanol solutions, nitric acid solutions, and various other reagents, such as Nital's reagent, Klemm's reagent, Kroll's reagent, Marble's reagent, and Vilella's reagent. Essentially any metal that can provide the necessary structural framework for a scaffold template that can also be etched and removed by an etchant that does not deleteriously affect the chemical and mechanical properties of the cross-linked, liquid crystal-containing polymeric scaffold, can be used.

Accordingly, it will be appreciated that by etching the metal foam scaffold template embedded within the cross-linked, polymeric scaffold and removing it, a polymeric scaffold containing liquid crystals and having interconnected pores where the metal foam scaffold template was removed is provided. Accordingly, it will be appreciated that the diameter of the interconnected pores of the polymeric scaffold is determined by the thickness of each metal fiber forming the metal foam scaffold template. Those interconnected pores are essentially the same diameter as the thickness of the metal used in forming the metal foam scaffold template.

Where the "dipping" step has been used, it will be further appreciated that the resultant crosslinked polymeric scaffold not only includes interconnected pores from where the metal foam scaffold template has been etched and removed, but the polymeric scaffold will also have interconnected channels provided where the voids or interstices of the metal foam scaffold template previously existed. That is, because of the dipping (i.e., immersion and removal) of the metal foam scaffold template, not all of the voids of the metal foam scaffold template are taken up by the crosslinked liquid crystal-containing scaffold. This creates a vascular network-like structure that allows cells and their nutrients and wastes to flow through not only the interconnected pores formed by etching and removal of the metal foam scaffold template, but also to flow through the interconnected channels outside of the "vessels" of the crosslinked liquid crystal-containing scaffold.

BRIEF DESCRIPTION OF THE DRAWINGS

These and other features and advantages of the present invention will become better understood with regard to the following description and accompanying drawings wherein.

DETAILED DESCRIPTION OF THE INVENTION

Figure 1:
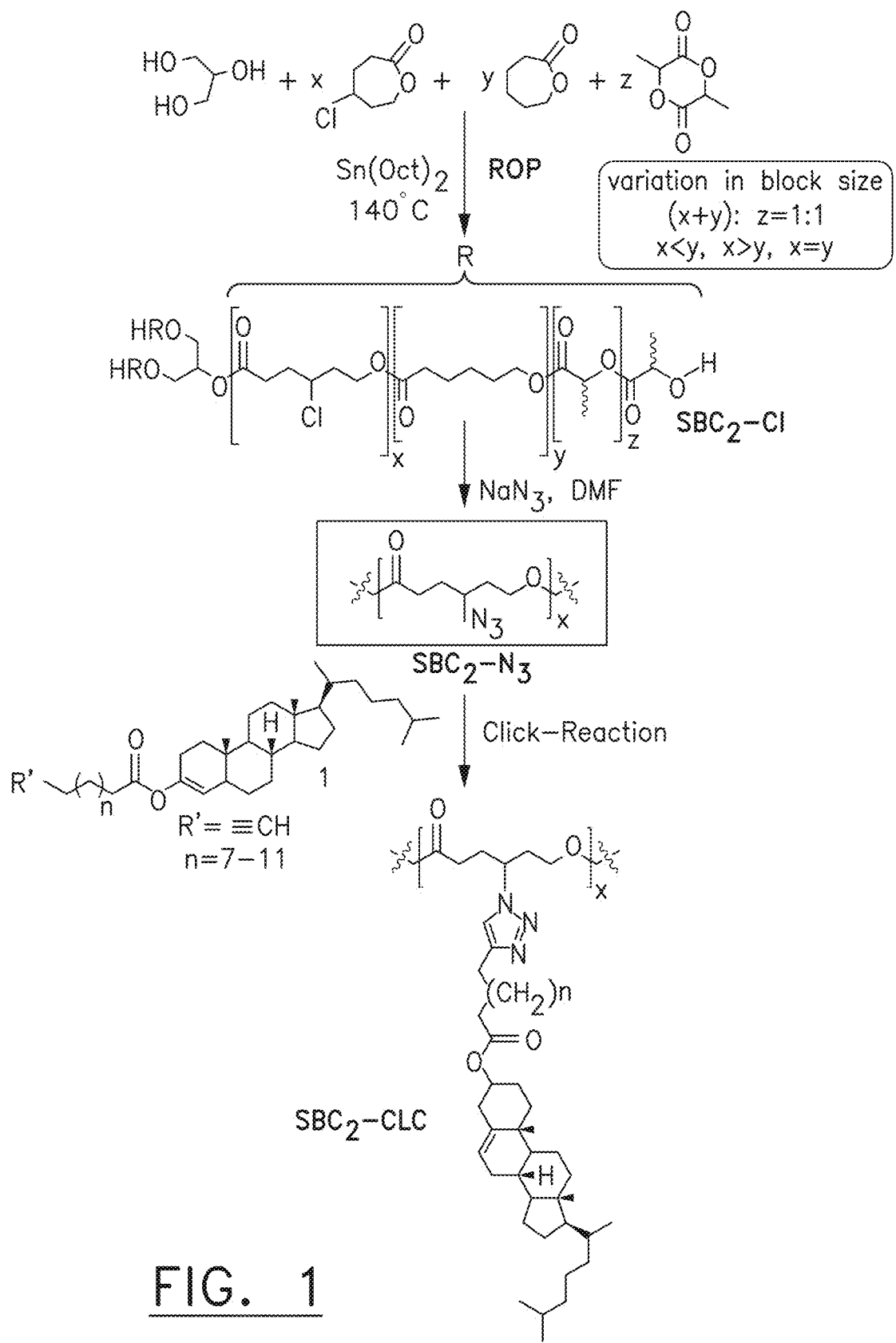
FIG. 1 is a reaction scheme of a synthetic pathway to star block copolymers (SBCs) that are used for the preparations of smart responsive scaffold (SRS) materials with pendant biocompatible cholesterol liquid crystal side chains, in accordance with the concepts of the present invention.
Figure 2:
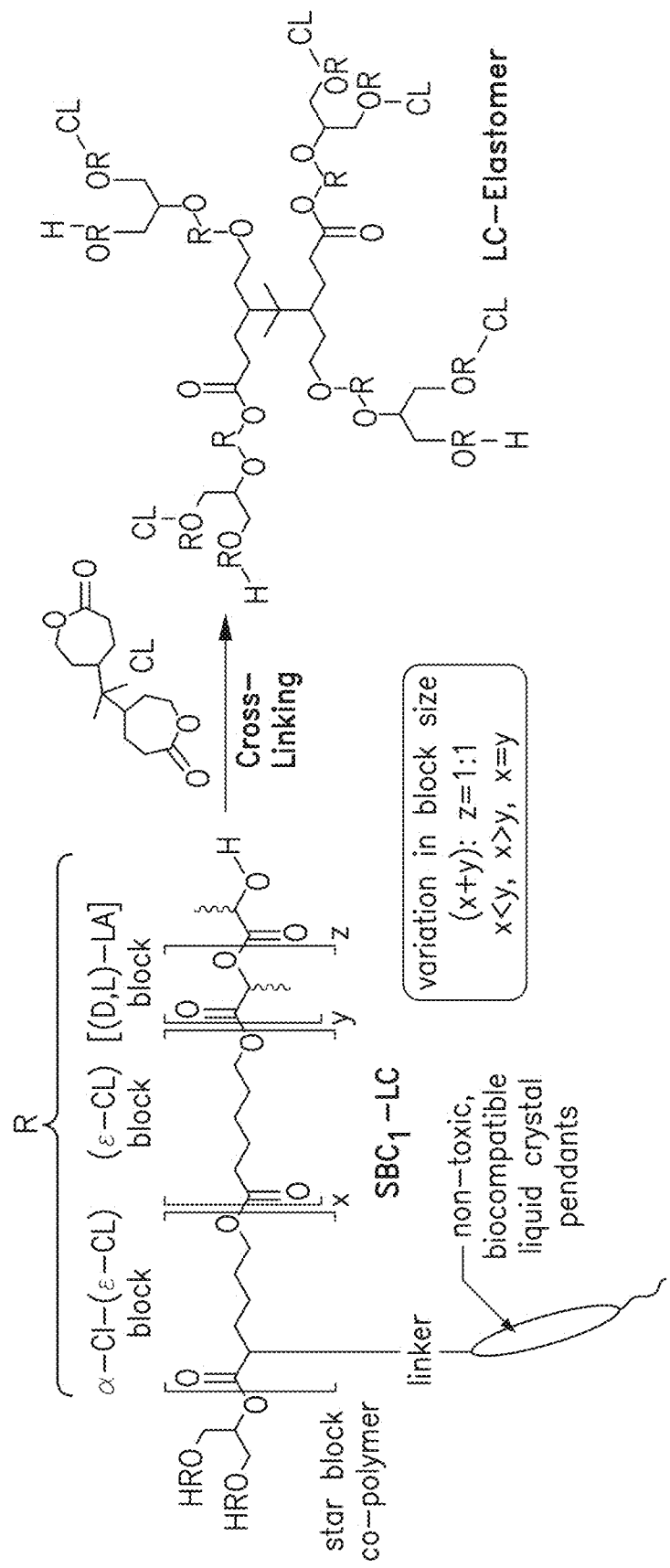
FIG. 2 is a simplified molecular structure of poly(ε-caprolactone)-co-(D,L)-lactide liquid crystal elastomers that is used as smart responsive scaffold (SRS) materials (bottom) obtained from star block copolymers (SBCs) with various liquid crystal pendant groups in accordance with the concepts of the present invention.
Figure 3A:
FIG. 3A is a scanning electron microscope (SEM) image of a nickel foam template in accordance with the concepts of the present invention.
Figure 3B:
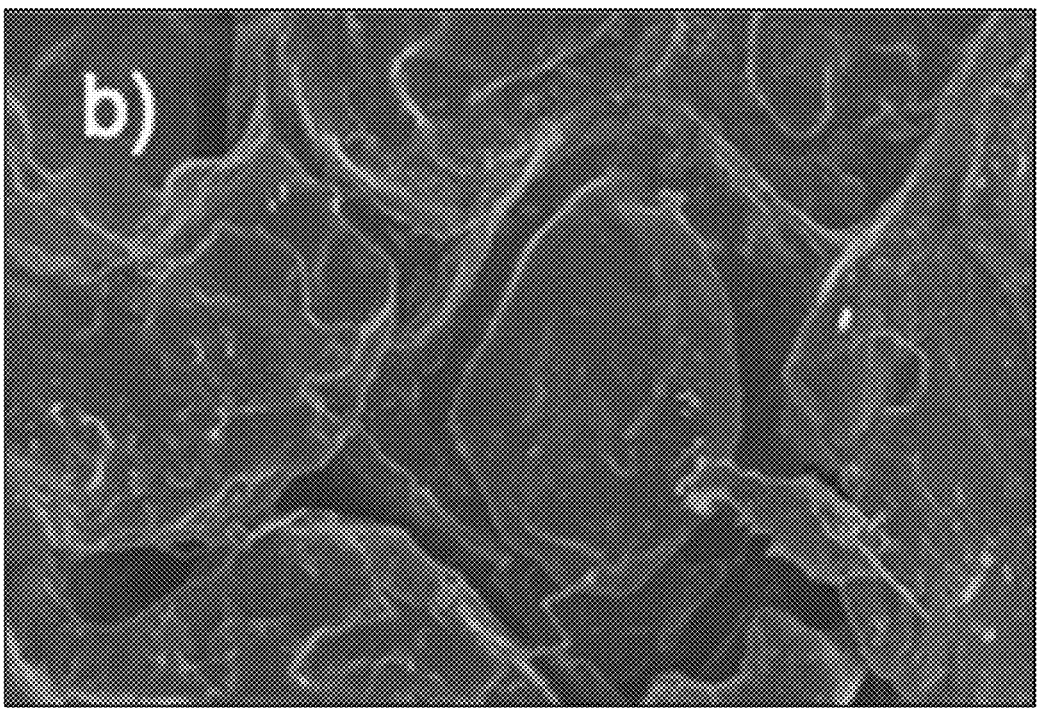
FIG. 3B is a scanning electron microscope (SEM) image of $SBC_1$-LC elastomer showing fully interconnected pores with an average pore size of about 100 μm and 150 μm at intersections in accordance with the concepts of the present invention.
Figure 3C:
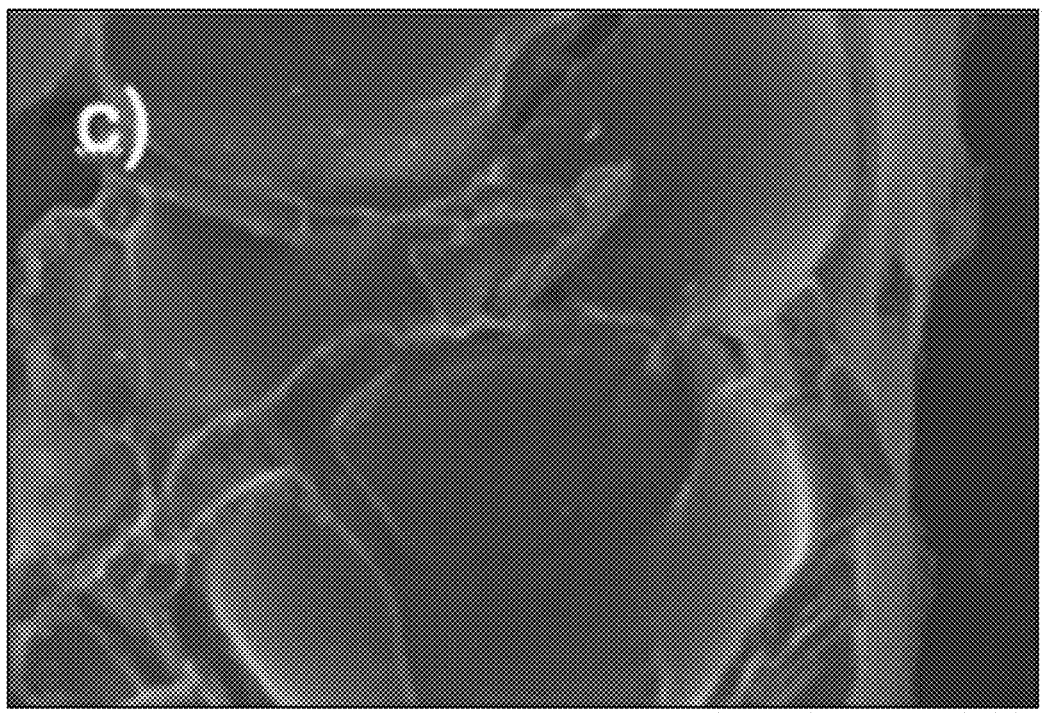
FIG. 3C is another scanning electron microscope (SEM) image of $SBC_1$-LC elastomer showing fully interconnected pores with an average pore size of about 100 μm and 150 μm at intersections in accordance with the concepts of the present invention.
Figure 3D:
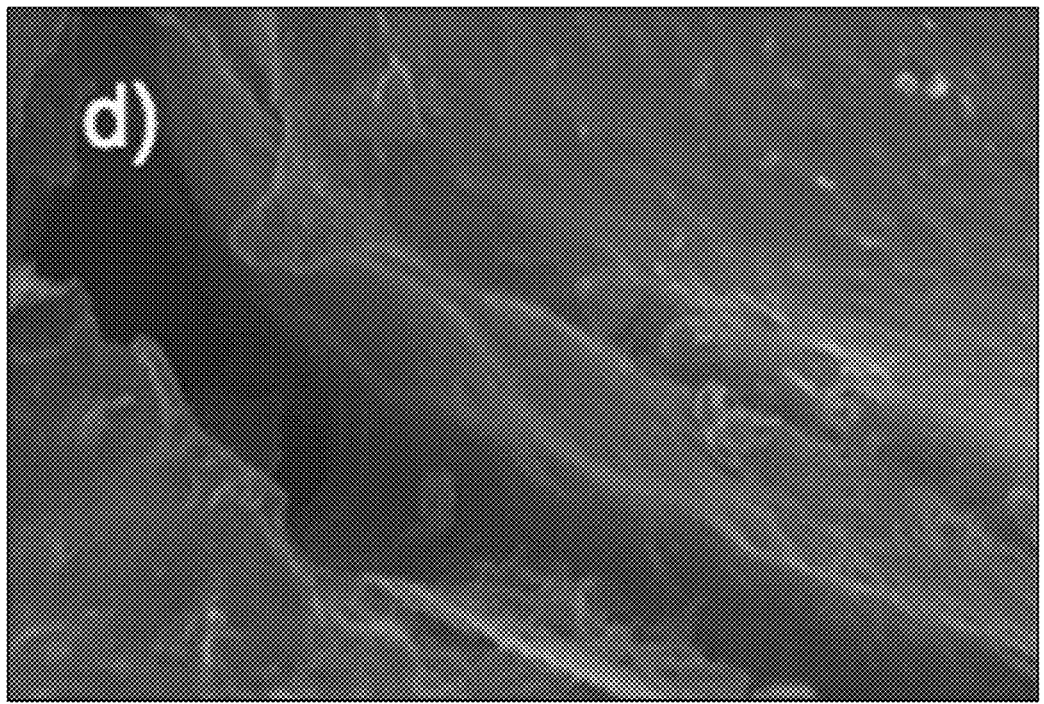
FIG. 3D is still another scanning electron microscope (SEM) image of $SBC_1$-LC elastomer showing fully interconnected channels with an average pore size of about 100 μm and 150 μm at intersections in accordance with the concepts of the present invention.

The synthesis and use of highly-functional liquid crystal elastomers for smart responsive scaffold (SRS) materials of the present invention are based on star block copolymers (SBCs) with a polyol such as glycerol as a central node or core, from which arms of random blocks of ring-opened, ε-caprolactone-, α- or γ-halogen substituted ε-caprolactone-, and (D,L)-lactide-based polyester units extend. The general reaction scheme is shown in FIG. 1. Smart responsive scaffolds (SRS) that are obtained in this fashion are then cross-linked to obtain a liquid crystal elastomer, SBC-LC-Elastomer, as shown in FIG. 2.

With regard to the synthesis of the star block copolymers (SBCs), there are three types of ring opening compounds for forming the arms of the SBCs. The first type is substituted lactones, such as α- or γ-halide-substituted ε-caprolactone, wherein the substituted group is a chlorine atom or a bromine atom. In FIG. 1, the number of repeat units derived from the halide-substituted ε-caprolactone is denoted by the letter "x".

α- or γ-halide-substituted ε-caprolactones are not commercially available and must be first produced. In particular, α-halide-substituted ε-caprolactone (designated herein as "α-Cl-ε-CL," as the halogen is most often chloride, but can be bromide) was prepared following procedures well known in the art and included in publications such as *Macromol. Biosci.*, 2014, DOI: 10.1002/mabi.201400325, the disclosure of which is incorporated herein by reference. Specifically, in one exemplified embodiment, 2-chlorocyclohexanone (10 g, 75.0 mmol) was dissolved in dry dichloromethane (15 mL). The oxidizing agent, meta-chloroperbenzoic acid (m-CPBA) (20 g, 115 mmol), was dissolved in dry dichloromethane (15 mL), and it was added to the 2-chlorocyclohexanone solution. The reaction mixture was stirred under nitrogen for four days. The meta-chloroperbenzoic acid (m-CBA) by-product was precipitated by cooling the reaction mixture at about −20° C. for approximately one hour. The by-product was filtered, and the remaining solution was washed with saturated solutions of sodium sulfate, sodium bicarbonate, and sodium chloride. Then, the solvent was removed under reduced pressure, and the pale yellow viscous liquid was purified by distillation under reduced pressure. The main fraction was collected by distillation under reduced pressure at about 0.1 mmHg and at a temperature of approximately 90° C.

Similarly, γ-halide-substituted ε-caprolactone (designated herein as "γ-Cl-ε-CL,") was prepared following procedures well known in the art. Specifically, in one exemplified embodiment, 4-chlorocyclohexanone was synthesized by reacting 7-oxabycyclo[2.2.1]heptane with 37% aqueous hydrochloric acid, whereby the solution was stirred at room temperature. After three days, the solution was separated into two layers. The reaction was continued for six days. The resultant mixture was then saturated with sodium chloride and extracted with an excess of ether. The organic layer was washed with sodium bicarbonate solution and distilled water, then dried over anhydrous sodium sulfate, and filtered. Then, solvent was evaporated under reduced pressure to obtain a solid. The crude product was re-crystallized twice from hexane to obtain pure 4-chlorocyclohexanol. 4-chlorocyclohexanol (7.83 g, 57.9 mmol) was dissolved in about 100 ml of dichloromethane, pyridinium chlorochromate (18.82 g, 87.30 mmol) was added in portions, and reaction was stirred for approximately 18 hours at room temperature. The precipitate was filtered and washed profusely with dichloromethane. Next, the solvent was removed under reduced pressure and the residue that was obtained was dissolved in about 200 ml of ether. The precipitate that was formed was filtered and washed with about 50 ml of ether. The organic layer was washed three times with distilled water, dried under sodium sulfate, and filtered. The solvent was then removed under reduced pressure to obtain a light yellow oil as pure 4-chlorocyclohexanone. 4-bromocyclohexanone (1.56 g, 8 mmol), obtained by the oxidation of 4-chlorocyclohexanol with pyridinium chlorochromate (PCC), was dissolved in dichloromethane (20.0 mL). To this solution, m-CPBA (1.52 g, 8.8 mmol) was added, and the mixture was stirred at room temperature for about 24 hours. The m-CBA by-product was precipitated by cooling the reaction mixture to around −20° C. for approximately one hour. The by-product was filtered, and the remaining solution was washed with a saturated solution of sodium thiosulfate and sodium bicarbonate. Then, the organic phase was dried with sodium sulfate, and the solvent was evaporated under reduced pressure, leaving a light-yellow oil as product.

The second type of ring opening compound utilized in the present invention is non-substituted lactones, such as ε-caprolactone, or similar compounds, such as its isomers alpha, beta, gamma, and delta caprolactones. Preferred is ε-caprolactone, which is commercially available. In FIG. 1, the number of repeat units derived from ε-caprolactone and the like is denoted by the letter "y" in the formulation of the star block copolymer.

The third type of ring opening polymerization compound that is utilized to form the star block copolymers of the present invention is one or more lactide-based polyesters. The various types of lactides that can be utilized are known to the literature and to the art and are derived from lactic acid $CH_3$—CH(OH)—C(0)OH. Examples of such compounds include D-lactide and L-lactide, with D,L-lactide being preferred. In FIG. 1, the number of repeat units derived from the lactide-based polyesters is denoted by the letter "z" in the formulation of the star block copolymer.

Once the ring opening components for the synthesis of the star block copolymer are obtained, further processing can occur. As shown in FIG. 1, the star block copolymers of the present invention are made by the reaction of core polyols with ring opening compounds. The core polyols can have a total of from 2 to about 8, desirably, from about 3 to about 6, and, preferably, 3 or 4 hydroxyl groups with specific examples including glycerol, 2,2-bis(hydroxymethyl)-1,3-propanediol, i.e. pentaerythritol:

and 2-[[3-hydroxy-2,2-bis(hydroxymethyl)propoxy]methyl]-2-(hydroxymethyl)1,3-propanediol, i.e. dipentaerythritol:

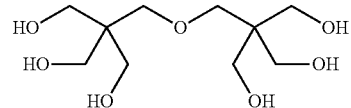

Glycerol is generally preferred.

The star block copolymers of the present invention can have different hydrophobicity that is controlled by an initial ratio of the blocks, e.g., x+y/z, wherein the two ε-caprolactone-based moieties (blocks x and y) are slightly more hydrophobic than the (D,L)-lactide segment (block z). The molar ratio of the x block to the y block is generally from about 0.1% to about 99%, and desirably from about 5% to about 70%, or from about 10% to about 50%, based upon the total molecular weight of the "x" blocks and the "y" blocks. The molar ratio of x+y to z is generally from about 1:9 to about 9:1, and desirably from about 1.5:1 to about 1:1.5, and preferably is about 1:1. The molar ratio percentage of x+y to the molar mass of the final elastomer can generally range from about 2% to about 99%, and preferably from about 5% to about 50%. The amount of the core polyol can be from about 0.001 g/mol to about 50 g/mol, desirably from about 0.1 g/mol to about 30 g/mol based upon the total molecular weight of said "x", said "y", and said "z". In FIGS. 1 and 2, while the pendant "HRO" groups are not set forth in detail for purposes of brevity, "R", is the star block copolymers as noted in each figure but wherein the number of repeat units of x, y, and z can independently be the same or independently different. Moreover, the order thereof outward from the initiating core polyol can also vary. Thus, it should be appreciated that numerous types of random star block copolymers are encompassed by the present invention.

The reaction of the core polyols with the three ring opening compounds are known to the art and to the literature. For example, glycerol can be mixed with the ε-caprolactone and the halide-substituted ε-caprolactone in any conventional manner, such as in a vortex mixer, for a short period of time and then the lactide-based polyester can be added thereto. These three compounds are then mixed and then the container can be flushed with nitrogen and placed in an oven until the lactide is completely melted. A tin catalyst such as tin(II) 2-ethylhexanoate is then added and mixed. The container can once again be flushed with nitrogen. The resulting star block copolymer liquid can then be recovered by dissolving it in dichloromethane and precipitating in a methanol dry ice bath.

In one exemplified embodiment, in a dry, silanized ampoule, glycerol (2.48 µl, 0.034 mmol) was mixed with ε-CL (3.62 g, 31.7 mmol) and α-Cl-ε-CL (0.5 g, 33 mmol), then mixed using a vortex mixer for about a minute, then, D,L-LA (7.21 g, 33.9 mmol) was added. The solution was mixed again using the vortex mixer, and the ampoule was then flushed with nitrogen and placed in the oven at about 120° C. until the D,L-LA completely melted. The contents were mixed in a vortex mixer, and tin(II) 2-ethylhexanoate (66 µl, 0.202 mmol) was added and mixed one last time. The ampoule was then flushed with nitrogen, flame-sealed under vacuum, and placed in a sand bath for about 48 hours at approximately 140° C. The seal was then broken, and the highly-viscous liquid was dissolved in dichloromethane. The solution was then poured into methanol and cooled using a dry ice/acetone bath at about −78° C. A white precipitate was obtained and was removed by filtration. The resultant product is star-poly(ε-CL-co-α-Cl-ε-CL-co-DL-LA) ($SBC_1$-Cl). It will be appreciated that star-poly(ε-CL-co-α-Br-ε-CL-co-DL-LA), ($SBC_1$-Br) was prepared utilizing the same procedure for preparing $SBC_1$-Cl, with the exception that α-Br-ε-CL was used instead of α-Cl-ε-CL. Similarly, star-poly(ε-CL-co-γ-Cl-ε-CL-co-DL-LA) ($SBC_2$-Cl) can be produced using γ-Cl-ε-CL instead of α-Cl-ε-CL and, likewise, γ-Br-ε-CL can be used instead of γ-Cl-ε-CL to provide star-poly(ε-CL-co-γ-Br-ε-CL-co-DL-LA) ($SBC_2$-Br).

Once the star block copolymer has been synthesized, it is reacted with suitable compounds that generally replace the halide atom of the substituted caprolactone compound (α- or γ-Cl-ε-CL). Suitable substitution of the halide atoms can be achieved by reacting the pendant halide atom of the block with various metal azide compounds, such as $NaN_3$, in suitable solvents such as DMF. For example, sodium azide can be reacted by reaction routes known to the art and to the literature, such as lead azide, silver and barium azides (which are shock sensitive detonators or rocket propellants), alkyl or aryl acyl azides or halide azides, such as chlorine, bromine and iodine azides or organic azides.

The Azide-Alkyne Huisgen Cycloaddition (or click reactions) reaction is a 1,3-dipolar cycloaddition that occurs between an azide and a terminal (in some other cases an internal) alkyne to give a 1,2,3-triazole (a five member ring). This reaction is best performed in the presence of a copper (I) catalyst. A Ruthenium catalyst is also widely used, as well as silver (I). The reaction conditions are as follows: the halide substituted star block copolymer is dissolved in dimethylform amide (DMF); and sodium azide is added to the solution and allowed to react overnight at room temperature in the presence of any of the catalysts mentioned above [mainly copper (I) iodide]. Reaction can also be carried at 35, 40, or 45° C. After that time DMF is removed, mixture is dissolved in toluene, the solution is centrifuged to remove the salt formed (dissolved in toluene). The toluene is evaporated to recover the purified product of click reaction.

As an example of the production of a suitable liquid crystal and the click reaction used to create the intermediate materials that lead to the liquid crystal elastomers of the present invention, cholesteryl 5-hexynoate was synthesized, whereby 5-hexynoic acid 3 g (26.7 mmol) and 130 mL dry dichloromethane were mixed in a round-bottom flask before it was cooled to about 0° C. using an ice bath, following another well-known procedure. In another round-bottom flask, cholesterol (10.3 g, 26.7 mmol), dicyclohexylcarbodiimide (8.28 g, 40 mmol), and 4-dimethylaminopyridine (0.2 g) were mixed. The 5-hexynoic acid solution was transferred stepwise to the flask that contained the cholesterol mixture, and the final mixture was maintained at about 0° C. for approximately one hour. Then, it was allowed to warm up to room temperature overnight. The resulting precipitate (dicyclohexylurea by-product) was removed by filtration and discarded. The filtrate was concentrated under reduced pressure, whereby the collected residue was dissolved in hexane solution. After evaporating hexane under reduced pressure, an excess of ethanol was added to the oily residue to collect the final product. An off-white solid was formed immediately, which was washed with ethanol. The solid product was dried under vacuum at about 50° C.

Next, the star-poly(ε-CL-co-α-cholesteryl 5-hexynoate-ε-CL-co-DL-LA), ($SBC_1$-CLC) was synthesized by click reaction. The click reaction was completed in a round-bottom flask where a 1 equivalent of $SBC_1$-$N_3$ (1.5 g, 33 mmol) was dissolved in freshly-distilled THF, then 1.2 equivalent of cholesteryl 5-hexynoate (1.94 g, 4.03 mmol), 0.1 molar equivalent of copper iodide (0.06 g, 0.33 mmol), and 0.1 molar equivalent of triethylamine (0.03 g, 0.33 mmol) were added. The mixture was stirred overnight at about 35° C. under nitrogen. Then, the solvent was evaporated under reduced pressure. The residual mixture was then dissolved in dichloromethane and was centrifuged to remove unreacted materials and side products.

Similarly, the star-poly(ε-CL-co-γ-cholesteryl 5-hexynoate-ε-CL-co-DL-LA), ($SBC_2$-CLC) was synthesized by click reaction. Again, this click reaction was completed in a round-bottom flask when $SBC_2$-$N_3$ (1.50 g, 0.700 mmol) was dissolved in 15 mL dry DMF. Then, cholesteryl 5-hexynoate (0.4 g, 0.832 mmol, 1.2 equiv), CuI (0.0132 g, 0.0690 mmol, 0.1 equiv.), and triethylamine (0.07 g/9.68 µL, 0.069 mmol, 0.1 equiv.) were added to the flask. The solution was stirred overnight at about 35° C. The reaction progress was monitored by infrared (IR) spectroscopy after about 24 hours. The disappearance of the azide band at 2096 $cm^{-1}$ indicated that the reaction was complete. The click reaction product was precipitated in cold methanol, filtered, and dried under reduced pressure.

All of the above reaction schemes are set forth in FIG. 1. It will be appreciated that any effective route for obtaining the liquid crystal elastomer of the present invention may also be used. It is noted herein that the present invention is generally directed to liquid crystal elastomers that are suitable for creating non-toxic, biocompatible smart response scaffolds. As such, the liquid crystals are pendant side chains to the elastomer and are non-toxic and biocompatible themselves. However, the present invention should not necessarily be limited to such liquid crystals, scaffolds and elastomers. As is to be seen, essentially any liquid crystalline composition capable of being immersed and coated onto a metal foam scaffold template and crosslinked, wherein the metal foam scaffold template can be etched and removed from the crosslinked scaffold, will be suitable for the present invention. The invention is not necessarily limited to biomedical applications, as other liquid crystal applications, such as security applications, may also use this technology. Thus, the present invention should be considered with a view toward the attached claims and not the embodiments provided herein.

In one desirable embodiment, however, pendant liquid crystals are utilized to impart a smart responsive property to the star block copolymers of the present invention. Again, the choice of liquid crystal pendants suitable for the functionalization of the star block copolymers used for SRS substrates is not necessarily limited to non-toxic, biocompatible liquid crystalline compounds, but is highly desirable. There are a number of classes of liquid crystals known to be non-toxic and biocompatible, such as cholesterol-based chiral nematic liquid crystals or any derivative thereof, or any cholesteryl liquid crystal or derivative thereof such as cholesteryl-5-hexynoate, or any sulfonated cholesteryl liquid crystal, or any 3,4-difluorophenyl-bicyclohexyl-based nematic liquid crystals or any derivative thereof. Examples of such suitable nematic cholesterol liquid crystals include the liquid crystals set forth in FIG. 1, wherein "n" is from about 7 to about 11. The synthesis of the cholesterol liquid crystal pendant starts from commercially available cholesterol, which is alkylated with 1,ψ-dihydroxyalkanes or 1,ψ-alkynols to give chiral nematic cholesteryl derivatives that can be incorporated into the SBCs. This can be accomplished either by esterification via a preceding atom transfer radical addition (ATRA) of 3-butenoic acid to the -chloro-caprolactone units, or by a Cu-catalyzed Huisgen 1,3-dipolar cycloaddition ("click" reaction) 24 after displacement of the chloro with an azide group next to the carbonyl group. Generally, any cholesterol related compound can be used as pendant groups that have been modified to contain other types of reactive groups as for example an ionic sulfonate group.

The smart responsive nature of these SRS materials is made by the use of pendant liquid crystal functional moieties wherein ordering and alignment can be manipulated using various substrates (commonly used for alignment of LC molecules in display devices), applied electric and magnetic fields, or mechanical deformation (stretching, twisting) to manipulate/steer direct differentiation of stem cells, control cell adhesion and growth rate, and potentially allow for simultaneous incorporation of oriented vascular networks, for example, by co-culturing of endothelial cells. In a quasi solvent-less, melt-polymerization at 140° C., which is easily be scaled up to considerable quantities, the hydrophilic-hydrophobic balance critical for cell attachment is easily controlled by the initial ratio of the building blocks (x+y/z), with the two ε-caprolactone-based moieties as hydrophobic and the (D,L)-lactide units as hydrophilic segment.

The degree of liquid crystal functionalization is controlled by the ratio between x and y, and determines both thermal and macroscopic liquid crystalline properties of the SBC and the final liquid crystal elastomer, in addition to the chiral properties when cholesteryl units are used (FIG. 1).

Enhancing the mobility (reducing steric constrains) of the liquid crystal pendant groups in the star block copolymer as well as the final elastomer is also possible by relocating their position on the SBC backbone using γ-Cl-ε-CL or γ-Br-ε-CL. In comparison to $SBC_1$ (based on α-Cl-ε-CL), in $SBC_2$ the liquid crystal pendants are attached in the center of the substituted halide-caprolactone block. As noted above, it is important that the three blocks (x, y, and z) are randomly distributed throughout the block copolymer arms. This reaction sequence could ultimately also provide more control over the number of liquid crystal pendants in the final elastomer since γ-halide-substituted caprolactone could be functionalized with the liquid crystal moiety prior to copolymerization, a path not accessible for α-Cl-ε-CL.

The polymeric star block copolymer compositions having pendant liquid crystal side chains (SBC-LC) having been produced, the compositions simply need to be crosslinked to provide a final liquid crystal elastomer. However, while prior inventions have done just that, the present invention seeks to provide improved smart responsive scaffolds (SRSs) that have significantly improved properties and consistently larger and interconnected pores. While the SRSs that are simply crosslinked to form elastomers, as set forth in WO 2014/172661, respond to external stimuli, such as temperature, elastic deformation (i.e. stress, strain), and applied electric and magnetic fields with an increase in ordering, and are a significant modification of polymeric scaffolds having liquid crystals, the smart responsive scaffolds of the present invention are believed to be an even more significant modification for inducing macroscopic ordering events through external stimuli, which is not possible with any other commercially-available scaffold. The biocompatible scaffolds of the present invention are able to respond to a variety of external stimuli, resulting in a macroscopic ordering event, which is then transduced to cells grown within. The biocompatibility of the elastomers has been evaluated by seeding cells and following their growth and expansion over desirable periods of time (e.g. several weeks). The porosity of the elastomers of the present invention is a key advantage, and the pore size can be tuned for a wide selection of cell sizes, thereby permitting the incorporation of growth factors, when needed, for enhancing cell viability and proliferation.

To accomplish this, the present invention uses metal foam, such as for example, commercial available nickel (Ni) foam, as a template during cross-linking to create a more porous liquid crystal (LC) elastomer film with interconnected pores, as shown in FIGS. 3A-3D. This ensures mass transport of nutrients to cells within the scaffolds, while also carrying cell waste away from the scaffolds, both of which are highly desirable, and provides for improvement in cell growth and adhesion. The internal morphology of the scaffold of the present invention also provides easy loading with other components that are required for a multitude of applications in sensing and security, whereby the load can be released or irreversibly allowed to leak out due to the application of a particular stress (i.e. when trying to modify or alter a product, such as in tamper-evident security systems).

It will be appreciated that the degree of cross-linking in the final liquid crystal elastomer can be controlled by the amount of cross-linker (e.g., bis-ε-caprolactone) added to the SBCs in this crosslinking step. The degree of cross-linking can be used to tune not only the thermal and mechanical properties of the SRS elastomers, but also the non-interconnected porosity of the LC elastomer, which will allow for integration (by swelling and soaking up) of collagen and growth factors. The choice of a hydrophilic cross-linker also aids the process of cell seeding and nutrient transport in the aqueous cell culture medium, but also allow one to enhance the non-interconnected porosity even further.

Crosslinkers or crosslinking agents include compounds that desirably are biocompatible and biodegradable with respect to the star block copolymer and include compounds such as 2,2-Bis(I-caprolactone-4-yl) propane (BCP) and derivatives thereof, and bis-caprolactone with oligoethylene glycol spacer and derivatives thereof.

For example purposes, the synthesis of 2,2-Bis(1-caprolactone-4-yl) propane (BCP) was conducted in two steps, following a well-known procedure for producing BCP. Initially, a flask was charged with 2-bis(4-hydroxy-cyclohexyl) propane (10.8 g, 45 mmol) and acetic acid (52 mL). Then, $CrO_3$ (11 g, 110 mmol) solution in acetic acid (50 mL) and distilled water (8 mL) was added dropwise over a period of about two hours to the previous flask, while maintaining the mixture temperature at between about 17 to 20° C. using an ice and water bath. After approximately 30 minutes, 2-propanol (50 mL) was added to an RB flask. The solution was stirred overnight. After about 24 hours, the dark purple solution was concentrated under reduced pressure, and a light purple solid was precipitated by the addition of distilled water to the flask. The crude product was filtered using a glass frit, and the solid material was washed multiple times with distilled water until a white solid material was obtained. Further purification by the crystallization in benzene yielded a solid material with a melting point that was compatible with the previously-reported number in the literature. In the next step, dry diketone (8.34 g, 35 mmol) was dissolved in dry dichloromethane (75 mL), and m-CPBA (6 g, 35 mmol) solution in dry dichloromethane (75 mL) was added to the flask. The mixture was refluxed for about 24 hours. Then, the m-CBA by-product was precipitated by cooling the reaction mixture to about −78° C. for approximately ten minutes. The by-product was filtered, and the remaining solution was concentrated under reduced pressure. The viscose crude product was washed with 2-heptanone, and the precipitate was dried under reduced pressure at about 50° C. overnight.

The cross-linking step produces the elastomers with either pendant cholesterol-based LC moieties, which would be regarded as side-chain LC-elastomers, or hydrophilic segments, depending on the starting polymer that was used. In one embodiment, elastomer mixtures may be prepared according to the synthetic routes demonstrated in FIG. 2. Basically the functionalized copolymers, either SBCs with liquid crystal side-chains or hydrophilic polymers with PEG segments in the main-chain, were mixed with crosslinker bis-caprolactone (BCL), ε-caprolactone monomer, and ring opening polymerization catalyst in a proper ratio and heated at 140° C. overnight under inert gas protection.

However, before crosslinking the SBC-LCs as set forth in FIG. 2, metal foam templates are prepared as template scaffolds. In one embodiment, nickel foam templates may be used and were cut into strips of 1.5 cm×3 cm or folded into rolls of 1 cm in diameter. SBC (modified or unmodified), BCP, and ε-caprolactone monomer were transferred into a flask and dissolved in chloroform. The mixture was then concentrated to a point that was right before the starting formation of white crystalline in the mixture. Tin(II) 2-ethylhexanoate catalyst (40 µl) was then added and well-mixed. The crosslinking mixture was then transferred into the containers which contained the Ni foam templates in specific shape. After a complete fill-up of the Ni foam channels with the polymer mixture, the Ni templates were either kept as is (immersed) or taken out from the polymer mixture (dipped) to drain off the polymer fill-ups in the channels. The oven was purged with $N_2$, and the temperature was increased and kept at 140° C. overnight. The resultant product was a crosslinked scaffold having a metal foam template scaffold embedded therein.

In a similar method, a 1×2×0.0015 cm (W×L×H respectively) rectangular shape of nickel foam was placed into an "aluminum bake pan" that was made specifically to tightly surround three of the sides of the nickel foam. The mold was set up on top of a glass slide. The star-poly(ε-CL-co-α-cholesteryl 5-hexynoate-ε-CL-co-DL-LA) was then prepared for crosslinking following Amsden's chemical cross-linking procedure to synthesize elastomers. In general, a 3:1 mass ratio of SBC:BCP and also a molar ratio of 2.3:1 for ε-CL:BCP were used. In a dry silanized ampoule, BCP (1 g) and of ε-CL (1 g) were mixed and heated in an oven or a sand bath to about 140° C. until the BCP was dissolved. Then, $SBC_1$-LC (3 g) was added to the ampoule, and the contents were mixed using a vortex mixer. Once the mixture was homogenous, tin(II) 2-ethylhexanoate catalyst (0.0324 mL) was added, and all contents of the ampoule were poured on top of the "aluminum bake pan" containing the nickel foam, making sure that all foam was fully covered with the mix. A glass slide was placed on top of the "aluminum bake pan" to close the system and was then placed in a temperature controlled oven at about 140° C. for approximately 18 hours. The resultant product is a crosslinked scaffold having a metal foam scaffold template embedded therein.

In order to remove the metal foam scaffold template, it must be etched away. Etching can be performed by any etchant that will adequately remove the metal foam scaffold template from the crosslinked polymeric scaffold. In one embodiment, the etching step may include removing the metal foam scaffold template by immersing the crosslinked scaffold in a saturated $FeCl_3$ solution. Such a solution is a known etchant and will remove metals such as nickel or iron oxide that forms the metal foam scaffold template from the crosslinked scaffold. Again, the metal foam template used should not be limited to nickel or iron oxide, as any metal or alloy can be used as the metal foam scaffold template, provided such a metal foam scaffold template can be produced and removed by a known etchant. Examples of possible metals or alloys other than the nickel and iron oxide metals noted above, which can be used include, but are not necessarily limited to, aluminum alloys, low and high carbon steel, brasses and bronzes, stainless stain, cast iron, tin alloys, copper alloys, zinc alloys, and ceramics. Correspondingly, there are a number of etchants that can be used instead of the proposed $FeCl_3$ solution above. These etchants include, but are not limited to, ammonia hydrogen peroxide solutions (used to etch copper alloys), $CuCl_2$ solutions, hydrochloric acid solutions, hydrofluoric acid solutions, ethanol solutions, nitric acid solutions, and various other reagents, such as Nital's reagent, Klemm's reagent, Kroll's reagent, Marble's reagent, and Vilella's reagent. Essentially any metal that can provide the necessary structural framework for a scaffold template that can also be etched and removed by an etchant that does not deleteriously affect the chemical and mechanical properties of the crosslinked, liquid crystal-containing polymeric scaffold, can be used.

Accordingly, it will be appreciated that by etching the metal foam scaffold template embedded within the crosslinked, polymeric scaffold and removing it, a polymeric scaffold containing liquid crystals and having interconnected pores where the metal foam scaffold template was removed is provided. Accordingly, it will be appreciated that the diameter of the interconnected pores of the polymeric scaffold is determined by the thickness of each metal fiber forming the metal foam scaffold template. Those interconnected pores are essentially the same diameter as the thickness of the metal used in forming the metal foam scaffold template.

Where the "dipping" step has been used, it will be further appreciated that the resultant crosslinked polymeric scaffold not only includes interconnected pores from where the metal foam scaffold template has been etched and removed, but the polymeric scaffold will also have interconnected channels provided where the voids or interstices of the metal foam scaffold template previously existed. That is, because of the dipping (i.e., immersion and removal) of the metal foam scaffold template, not all of the voids of the metal foam scaffold template are taken up by the crosslinked liquid crystal-containing scaffold. This creates a vascular network-like structure that allows cells and their nutrients and wastes to flow through not only the interconnected pores formed by etching and removal of the metal foam scaffold template, but also to flow through the interconnected channels outside of the "vessels" of the crosslinked liquid crystal-containing scaffold.

Figure 4:
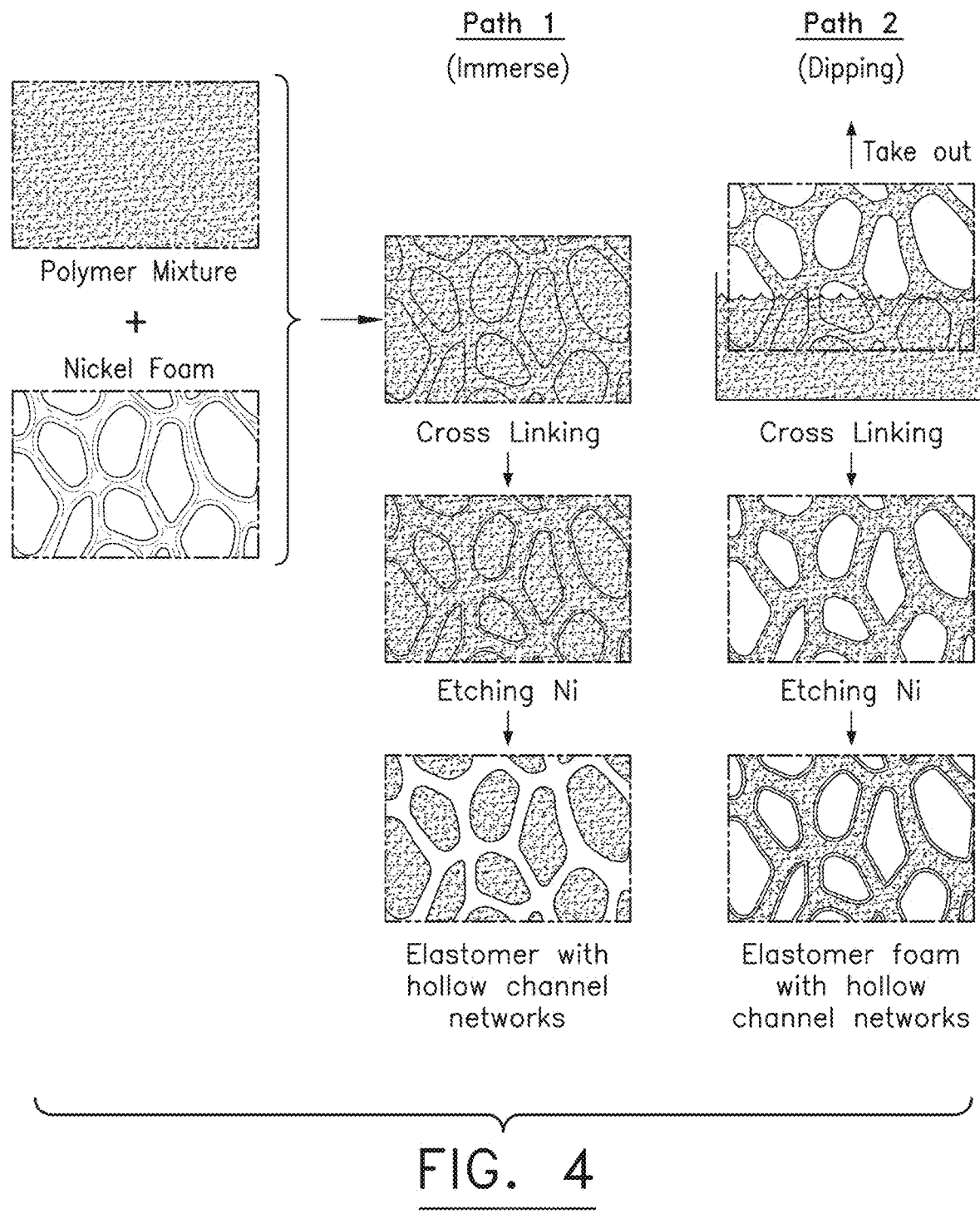
FIG. 4 is a schematic diagram showing the procedural steps for both methods of producing a polymeric scaffold containing liquid crystals and having interconnected pores, wherein one method provides a vessel in muscle like result, while the other method provides a vascular network like result.
Figure 5A:
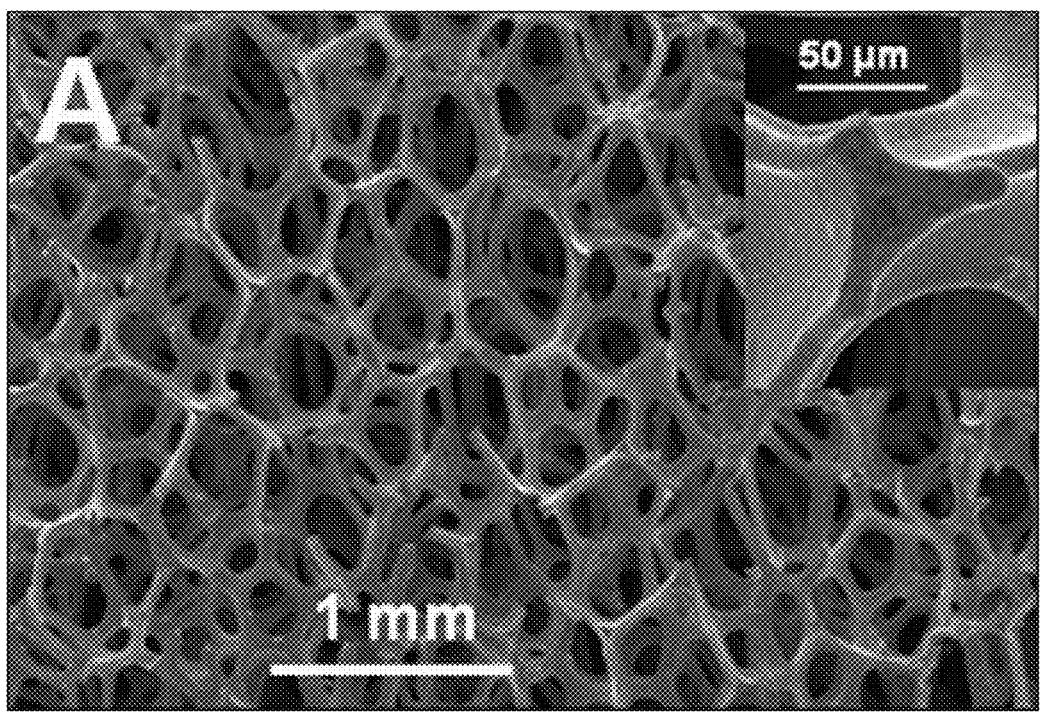
FIG. 5A is a scanning electron microscope (SEM) image of a nickel foam template in accordance with the concepts of the present invention.
Figure 5B:
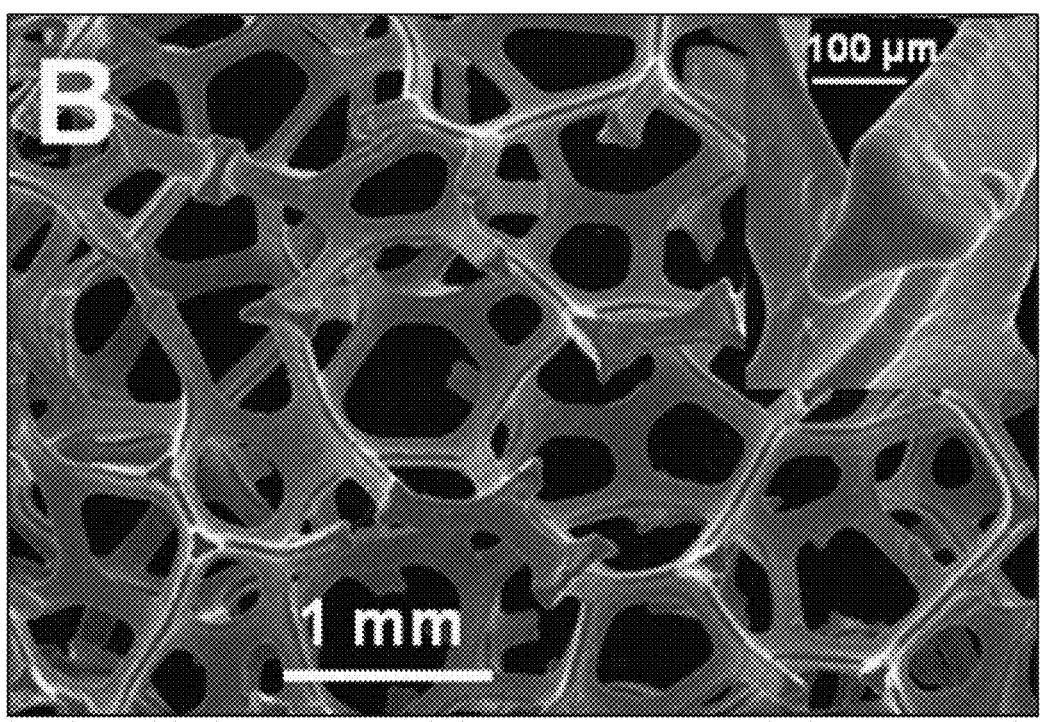
FIG. 5B is another scanning electron microscope (SEM) image of a nickel foam template in accordance with the concepts of the present invention.
Figure 5C:
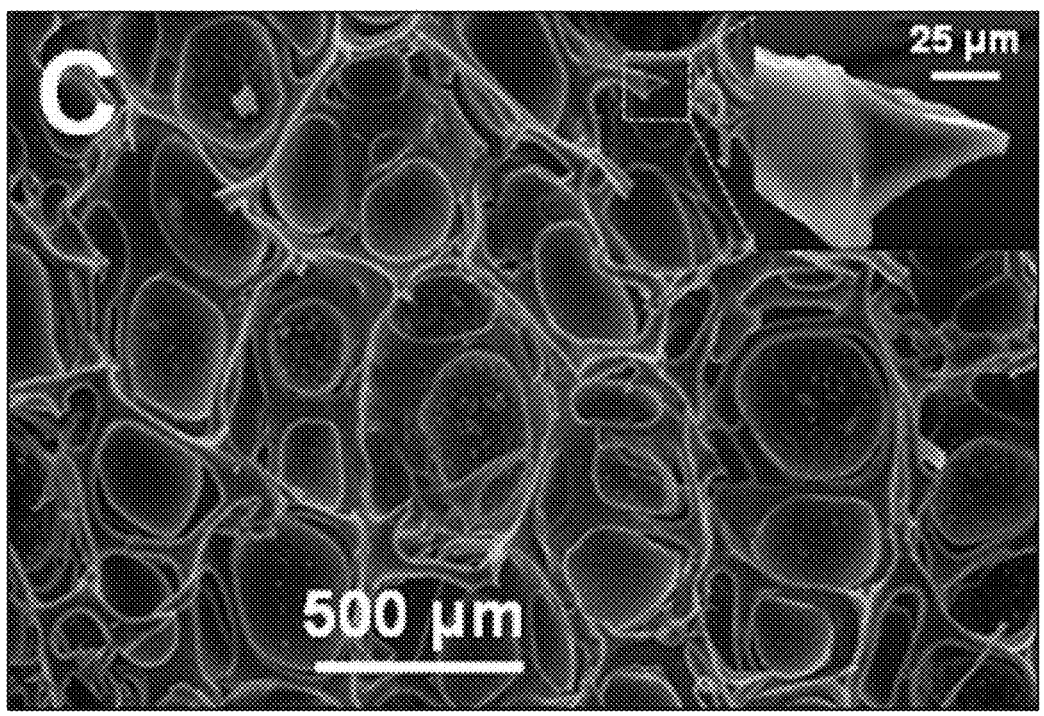
FIG. 5C is a scanning electron microscope (SEM) image of a resultant LC elastomer of the present invention having hollow vessels, as well as interconnecting channels.
Figure 5D:
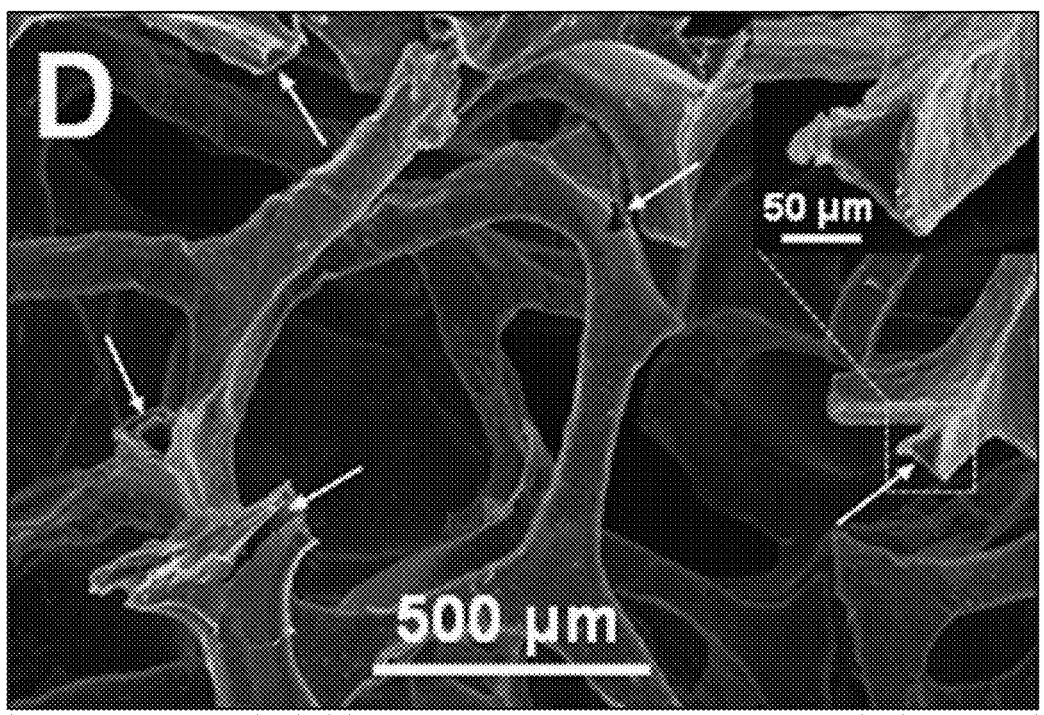
FIG. 5D is another scanning electron microscope (SEM) image of a resultant LC elastomer of the present invention having hollow vessels, as well as interconnecting channels.

It will be appreciated that a unique feature for the proposed use of the LC elastomers for 3D cell culture studies using scaffolds is the internal morphology of the elastomer materials. As shown the scheme in FIG. 4, the polymer/crosslinker mixtures were casted on the Ni foam before crosslinking. Then, there are two paths that the process may undertake in order to control the morphology of the elastomer products. First, following path 1 as shown in FIG. 4, the crosslinking occurs when the polymer mixtures has fully filled all the pores of the nickel or metal foam. After crosslinking, an edge of the Ni foam is exposed by scratching off the surface of the elastomer, whereupon the metal foam is etched out with the help of saturated $FeCl_3$ or other etchant solutions. Elastomers prepared in this way will embed a vessel-in-muscle like 3D channel network in the elastomer.

The second path shown in FIG. 4 is that after immersing the metal foam in the polymer mixtures for a period of time, such as about 1 to about 10 minutes and desirably about 4 to about 6 minutes, the nickel foam sacrificial template is taken out of the polymer mixture. This is called "dipping." However, due to its viscosity, at least a thin layer of the polymer mixture is left on the nickel surface of the nickel foam and covers the structural microframe of the metal foam. However, most of the channels or interstices in the metal or nickel foam are void of any polymer mixture after draining. The metal or nickel foam with the thin layer polymer cover is then heated and crosslinked. After etching-off of the embedded metal foam template frame, each micro-fiber of the crosslinked elastomeric scaffold that was built up on the nickel foam template is hollow, generating interconnected pores within the foams. These are considered secondary hollow 3D interconnected network pores. The structure of this novel 3D channel-network is similar to an interconnected vessel system that is wholly isolated from muscles and free-standing in vitro, which is unpractical for real vessel systems. Such elastomers prepared in this manner will provide an "isolated vascular-network like" 3D channel network in the elastomer.

The porosity and size of the interconnected channel network scaffold can be controlled by using metal foam templates of different sizes.

In one embodiment, nickel foam was removed by etching in saturated iron (III) chloride solution. The elastomeric foams were then washed with deionized water multiple times until the washing solution was clear. The obtained foams were then dried in air and characterized with a scanning electron microscope (SEM). In another embodiment, the resulting elastomer foam was removed from the oven and fully immersed into a beaker containing a saturated solution of $FeCl_3$ for five days and then washed with de-ionized water to remove all solids that formed as black powder. Elastomer foam was then washed with 70% ethanol solution to remove unreacted products and to prepare for biocompatibility tests, and dried under vacuum before analysis. The same procedure was followed for $SBC_2$-elastomer.

In FIGS. 3 and 5, various SEM images have been provided. In FIG. 3A, a SEM image of a nickel foam template in accordance with the concepts of the present invention is shown. In FIG. 3B, a SEM image of $SBC_1$-LC elastomer showing fully interconnected pores with an average pore size of about 100 μm and 150 μm at intersections in accordance with the concepts of the present invention in shown. This is an example of the vessel-in-muscle like structure produced using the "immersing" method of the present invention. In FIG. 3C another SEM image of $SBC_1$-LC elastomer showing fully interconnected pores with an average pore size of about 100 μm and 150 μm at intersections in accordance with the concepts of the present invention. This image also provides the structure produced using the "immersing" method. FIG. 3D is still another SEM image of $SBC_1$-LC elastomer showing fully interconnected channels with an average pore size of about 100 μm and 150 μm at intersections in accordance with the concepts of the present invention. In FIGS. 5A and 5B, SEM images of nickel foam templates in accordance with the concepts of the present invention are shown. In FIG. 5C, a SEM image of a resultant liquid crystal elastomeric scaffold of the present invention having hollow vessels (i.e., pores) as well as interconnecting channels is shown. This image provides the structure produced using the "dipping" method. FIG. 5D is another SEM image of a resultant polymeric smart response scaffold of the present invention having hollow vessels (i.e., pores) as well as interconnecting channels. Again, this image provides the structure produced using the "dipping" method.

It should also be appreciated that in other embodiments, the present invention may be prepared using any polymeric composition that does not use liquid crystal side chains.

Thus, it can be seen that the objects of the present invention have been satisfied by the scaffold and its method for production as presented above. While in accordance with the Patent Statutes, only a few preferred embodiments have been presented and described in detail. It should be understood that the invention is not limited thereto and thereby, and any conflict regarding the scope of the invention should be provided in view of the scope of the attached claims.

What is claimed is:

1. A polymeric scaffold having interconnected pores and comprising a plurality of cross-linked star block copolymers, each star block copolymer having a plurality of pendant liquid crystal side chains.

2. The polymeric scaffold as claimed in claim 1, wherein each cross-linked star block copolymer comprises:
   a core derived from a polyol; and
   a plurality of arms of random block copolymers comprising:
      one or more polymer blocks derived from halide-substituted lactone monomers;
      one or more polymer blocks derived from lactone monomers or isomers thereof; and
      one or more polymer blocks derived from lactide monomers,
      wherein at least one of the one or more polymer blocks derived from the halide-substituted lactone monomers of each arm contains a liquid crystal pendant from the polymer block at the position where the halide was originally substituted.

3. The polymeric scaffold as claimed in claim 1, wherein the interconnected pores have a diameter ranging from about 100 microns to about 500 microns.

4. The polymeric scaffold as claimed in claim 1, wherein the scaffold is elastomeric.

5. The polymeric scaffold as claimed in claim 1, wherein the scaffold is biocompatible.

6. The polymeric scaffold as claimed in claim 1, wherein the scaffold is biodegradable.

7. The polymeric scaffold as claimed in claim 2, wherein the liquid crystal is selected from the group consisting of a cholesterol-based chiral nematic liquid crystal and derivatives thereof, a cholesteryl liquid crystal and derivatives thereof; and a 3,4-difluoropentyl-bicyclohexyl-base nematic liquid crystal and derivatives thereof.

8. The polymeric scaffold as claimed in claim 1, wherein the polymeric scaffold further includes a plurality of pores that are not interconnected, and that range in diameter of from 5 microns to 500 microns.

9. The polymeric scaffold as claimed in claim 1, wherein said cross-linked star block polymers are crosslinked using a compound that is biocompatible and biodegradable with said star block copolymers.

10. The polymeric scaffold as claimed in claim 9, wherein said compound is selected from the group consisting of 2,2-Bis(1-caprolactone-4-yl) propane (BCP) and derivatives thereof, and Bis-caprolactone with oligoethylene glycol spacer and derivatives thereof.

11. The polymeric scaffold as claimed in claim 1, wherein the polymeric scaffold includes interconnected pores and interconnected channels, the interconnected pores forming hollow passages within the framework of the polymeric scaffold.

12. The polymeric scaffold as claimed in claim 1, wherein the scaffold is adaptable for use in combination with stem cells for tissue engineering and cell delivery.

13. The polymeric scaffold as claimed in claim 1, wherein the scaffold is a biocompatible, smart responsive scaffold responsive to external stimuli.

14. A method for the production of a polymeric scaffold having interconnected pores and comprising a plurality of cross-linked star block copolymers, each star block copolymer having a plurality of pendant liquid crystal side chains, the method comprising:
providing a metal foam scaffold template;
casting a liquid crystal-containing polymeric material around the metal foam scaffold template;
crosslinking the casted liquid crystal-containing polymeric material and metal foam scaffold template to provide a polymeric scaffold around the metal foam scaffold template to form a crosslinked scaffold; and
etching the metal foam scaffold template to remove the metal foam scaffold template embedded within the crosslinked scaffold and to provide a polymeric scaffold and having interconnected pores and comprising a plurality of cross-linked star block copolymers, each star block copolymer having a plurality of pendant liquid crystal side chains, where the metal foam scaffold template was removed.

15. The method as claimed in claim 14, wherein the step of casting includes the step of dipping the metal foam scaffold template into the liquid crystal-containing polymeric material.

16. The method as claimed in claim 15, wherein the step of casting further includes removing the metal foam scaffold template from the liquid crystal-containing polymeric material before completely crosslinking so as to provide channels within the polymeric scaffold upon crosslinking, the channels being defined by the voids within the metal foam scaffold template.

17. The method as claimed in claim 14, wherein the step of casting includes the step of immersing the metal foam scaffold template into the liquid crystal-containing polymeric material.

18. The method as claimed in claim 14, wherein the step of casting includes the step of pouring the liquid crystal-containing polymeric material over the metal foam scaffold template.

19. The method as claimed in claim 14, wherein the step of crosslinking includes crosslinking with a crosslinking agent to form a thermoset elastomer, wherein the crosslinking agent is selected from the group consisting of 2,2-bis (1-caprolactone-4-yl) propane (BCP) and derivatives thereof, and bis-caprolactone with oligoethylene glycol spacer and derivatives thereof.

20. The method as claimed in claim 19, wherein the step of crosslinking further includes heating the casted liquid crystal-containing polymeric material and metal foam scaffold template to at least 140° C.

21. The method as claimed in claim 14, wherein the step of etching including removing the metal foam scaffold template by immersing the crosslinked scaffold in a saturated etchant solution.

22. The method as claimed in claim 21, wherein the etchant solution is a $FeCl_3$ solution.

23. The method as claimed in claim 14, wherein each star block copolymer comprises:
a core derived from a polyol; and
a plurality of arms of random block copolymers comprising:
one or more polymer blocks derived from halide-substituted lactone monomers;
one or more polymer blocks derived from lactone monomers or isomers thereof; and
one or more polymer blocks derived from lactide monomers,
wherein at least one of the one or more polymer blocks derived from the halide-substituted lactone monomers of each arm contains a liquid crystal pendant from the polymer block at the position where the halide was originally substituted.

24. The method as claimed in claim 14, wherein the diameter of the interconnected pores of the polymeric scaffold is determined by the thickness of each metal fiber forming the metal foam scaffold template.

25. The method as claimed in claim 14, wherein the metal in the metal foam scaffold template is nickel or iron oxide.

26. The polymeric scaffold as claimed in claim 1, wherein the pendant liquid crystal side chains are biocompatible.

* * * * *